United States Patent [19]

Manda

[11] Plant 4,592

[45] Sep. 16, 1980

[54] **VITACEAE; *CISSUS RHOMBIFOLIA* NAMED MANDA'S COMPACTA**

[75] Inventor: Albert W. Manda, Short Hills, N.J.

[73] Assignee: W. A. Manda Inc., Livingston, N.J.

[21] Appl. No.: 964,659

[22] Filed: Nov. 29, 1978

[51] Int. Cl.[2] ..... A01H 5/12

[52] U.S. Cl. ..... Plt./88

[58] Field of Search ..... Plt./88

*Primary Examiner*—Robert E. Bagwill

*Attorney, Agent, or Firm*—W. A. Snow

[57] ABSTRACT

A new variety of *Cissus rhombifolia* plant distinguished by its profuse nodes, vigorous strength and growing habit, ability to be grown using only one cutting per pot, closer spacing of leaves, lesser inclination to damage, and lesser aptitude to show disease damage as new shoots are readily present or grow readily from nodes which have lost leaves.

2 Drawing Figures

BACKGROUND OF THE INVENTION

This new variety of *Cissus rhombifolia* originated from cuttings made by me during breeding efforts carried on at the W. A. Manda, Inc. greenhouse in Livingston, N.J., since August 1977 with the object of producing improved *Cissus rhombifolia* and *Cissus rhombifolia* "Mandaiana" for the commercial market. This plant was discovered by me in August 1977 in a large bed of *Cissus rhombifolia* plants and because it appeared to possess the most desirable characteristics of its parent, as well as shorter internodes resulting in closer spaced leaves, making it appear fuller, and because it was fast growing, and because of its vigor and because new shoots were either present or growing readily from nodes which had at least three leaves, this new variety was asexually reproduced by me and under my direction at Livingston, N.J., and successive generations have shown that the novel characteristics of the new variety are fixed and hold true, in all respects, from generation to generation.

DESCRIPTION OF THE DRAWING

This new *Cissus rhombifolia* plant is illustrated by the accompanying drawing, in which the upper view shows a potted plant while the lower view shows the upper faces of a cluster of three leaves, the color shown being painted on the photograph to bring out the true color.

DESCRIPTION OF THE NEW PLANT VARIETY

The following is a detailed description of my new variety of *Cissus rhombifolia* plant, with color designations according to The R.H.S. Colour Chart published by The Royal Horticultural Society of London, England.

THE PLANT

Origin: Cuttings.

Parentage: *Cissus rhombifolia.*

Classification:

*Botanic.*—Vitaceae: *Cissus rhombifolia* "Manda's Compacta".

*Commercial.*—Manda's Compact Grape Ivy.

Form: Herbaceous vine.

Shape: Upright when young; trailing when mature unless staked.

Growth rate: Vigorous; upright, compact, self-branching and sturdy with good strength.

Branches:

*Angle of attachment.*—Approximately 45°.

*Spacing.*—Branches from central stem ¾ inch to 1½ inches at full growth.

Foliage: Quantity — Abundant.

*Leaves.*—Shape: Pinnately compound. Size: Width and length — approximately ¾ inch to 5¼ inches depending on culture. Margin Type: Many pronounced teeth. Texture: Almost leathery. Gloss: Shiny, like polished wax. Smooth: Yes. Pubescence distribution: White on new growth; white on under side of leaf but disappears on upper surface when leaf matures. Color: Upper side young growth — light green 135A. Under side — light dull green 138A and at mature growth develops a slight brown cast from pubescence. Leaflets: Rhombic ovate with pronounced upward arching between veins. Size: Approximate length — ¾" when immature to 4 inches. Approximate width — ¾" to 4". Shape: Pinnately compound. Petioles: Length including rachis — approximately ½" to 2". Rachis: Almost none to ⅞". Ribs and veins: Pinnate; light green to brown on mature leaves.

FLOWER BUDS

Cissus flowers infrequently except when very mature. *Cissus rhombifolia* "Manda's Compacta" has not yet flowered.

This new variety of *Cissus rhombifolia* is a vigorous grower, hardy as observed at Livingston, N.J. The plant is readily grown for raising in cell packs because of its bushy habit. The plant is readily salable because of the closer spacing of the leaves and is more attractive and appears fuller than other varieties. It is more vigorous as new shoots are either present or grow more readily from nodes which have lost their leaves. The plant is outstanding.

| | MEASUREMENTS | | |
|---|---|---|---|
| | Manda's Compacta | Mandaiana | Cissus Rhombifolia |
| Distance Between Nodes: | ¼" to 3½" | ½" to 6" | ½" to 5¼" |
| Leaf Size (Mature): Length Including Petiole: | 1¼" to 6" | 2½" to | 2½" to |

-continued

| | MEASUREMENTS | | |
|---|---|---|---|
| | Manda's Compacta | Mandaiana | Cissus Rhombifolia |
| | | 8½" | 6¾" |
| Width: | ¾" to 5¼" | 1⅜" to 3" | 1¼" to 5½" |
| Leaflet Size (Mature): | | | |
| Length Including Petiole: | ¾" to 4" | ¾" to 5" | ⅞" to 4¼" |
| Width: | ¾" to 3" | ⅞" to 5" | 9/16" to 2⅝" |
| Petiole Length: | ⅜" to 2" | 1¼" to 4⅝" | 11/16" to 2½" |
| Rachis Length: | Almost none | Almost none | 1/16" to ⅞" |

-continued

| | MEASUREMENTS | | |
|---|---|---|---|
| | Manda's Compacta | Mandaiana | Cissus Rhombifolia |
| | to ⅞" | to 1 3/16" | |

the above dimensions are approximate and the above dimensions were taken from varieties grown under greenhouse conditions in the greenhouse of W. A. Manda, Inc. in Livingston, N.J. The above measurements could vary under different cultural conditions.

I claim:

1. A new and distinct variety of *Cissus rhombifolia,* substantially as herein shown and described, characterized by its self-branching and compactness, closer spacing of nodes and having a shiny leaf, vigorous growing habit in less time and space, less prone to damage, and easier propagation and lesser inclination to damage while in retail outlets.

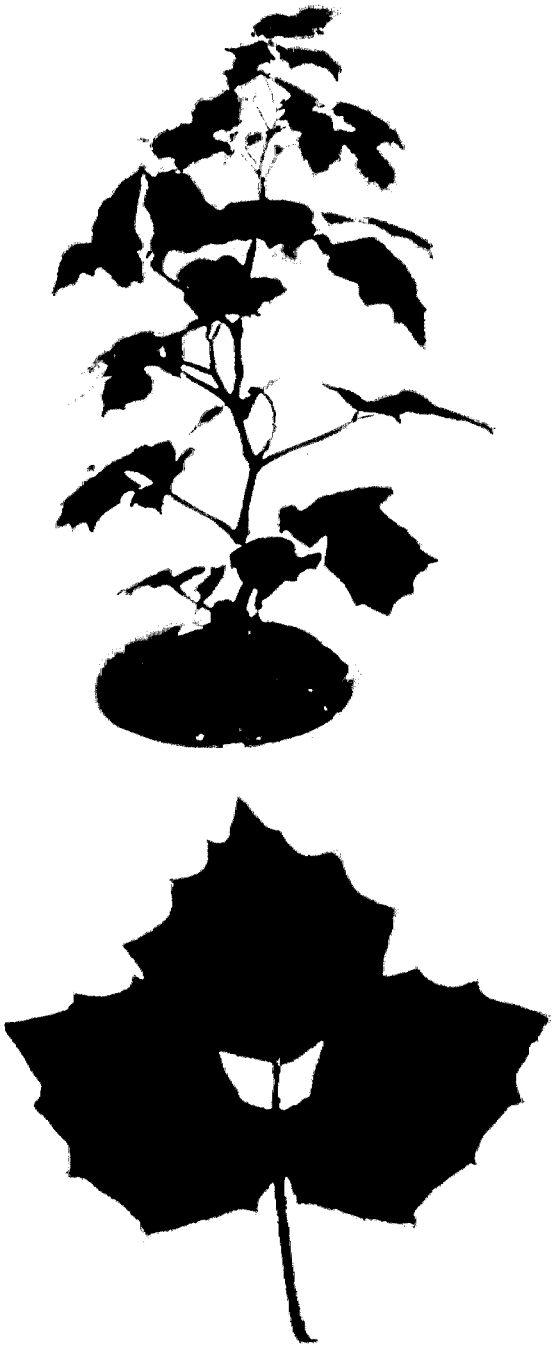

* * * * *